United States Patent [19]

Hagedorn

[11] 3,994,963

[45] Nov. 30, 1976

[54] SCHAEFFER SALT PURIFICATION

[75] Inventor: Donald W. Hagedorn, Succasunna, N.J.

[73] Assignee: American Cyanamid Company, Stamford, Conn.

[22] Filed: Feb. 28, 1975

[21] Appl. No.: 554,032

[52] U.S. Cl............................................. 260/512 C
[51] Int. Cl.$^2$...................................... C07C 143/42
[58] Field of Search................................ 260/512 C

[56] References Cited
UNITED STATES PATENTS

| | | | |
|---|---|---|---|
| 1,494,096 | 5/1924 | Berlin et al. | 260/512 C |
| 1,880,442 | 10/1932 | Helfaer | 260/512 C |
| 3,875,216 | 4/1975 | Feldman et al. | 260/512 C |

FOREIGN PATENTS OR APPLICATIONS

| | | | |
|---|---|---|---|
| 1,341,351 | 12/1973 | United Kingdom | 260/512 C |

*Primary Examiner*—Bernard Helfin
*Assistant Examiner*—Nicky Chan
*Attorney, Agent, or Firm*—John L. Sullivan

[57] ABSTRACT

A process for recovering purified Schaeffer's Salt from a sulfonation mixture is disclosed wherein unreacted 2-naphthol is removed by activated carbon treatment, 6,6'-oxybis(2-naphthalene sulfonic acid) is selectively removed as the disodium salt at a pH above about 9, and Schaeffer's salt is then salted out at a pH in the range of 2–7.

12 Claims, No Drawings

SCHAEFFER SALT PURIFICATION

This invention relates to an improved method for the recovery of Schaeffer's Salt from a sulfonation mixture containing the free acid. More particularly, this invention relates to such a process wherein the sodium salt of 6,6'-oxybis(2-naphthalene sulfonic acid) an undesirable by-product is removed from the Schaeffer's Salt.

Schaeffer's Salt is an important chemical intermediate, primarily used in the manufacture of dyestuffs. Of the many dyes which are made from Schaeffer's Salt, there may be mentioned, for example, C.I. Acid Orange 12 (C.I. 15970), C.I. Acid Red 115 (C.I. 27200), C.I. Acid Black 26 (C.I. 27070), C.I. Direct Violet 47 (C.I. 25410), and C.I. Food Orange 3 (C.I. 15985).

Various methods used in the past to prepare Schaeffer's Salt have been unsatisfactory because the resulting Schaeffer's Salt is contaminated with unreacted 2-naphthol (BN), by-product 6,6'-oxybis(2-naphthalene sulfonic acid) (DONS), and by-product 2-naphthol-3,6-disulfonic acid (R-acid).

In the conventional method for preparing Schaeffer's Salt, 2-naphthol is heated with concentrated sulfuric acid until sulfonation is complete. The temperature and reaction time are controlled to provide a high yield of 2-naphthol-6-sulfonic acid. The sulfonation mass is then drowned in water, the resulting solution is neutralized with sodium hydroxide or sodium carbonate, and the crude Schaeffer's Salt is isolated by filtration. The Schaeffer's Salt thus obtained is not pure enough for commercial use and, therefore, must be purified. The conventional method for doing this is to recrystallize the Schaeffer's Salt by dissolving the crude salt in water, treating the solution with activated carbon and, optionally, filter aids, clarifying the solution by filtration, salting out the Schaeffer's Salt by addition of common salt to the clarified solution, and filtering off the precipitated Schaeffer's Salt. Thus, the conventional recovery and purification of the salt requires many operations, including three filtration steps. The many operations thus involved have a serious adverse effect on the cost of manufacture of Schaeffer's Salt. Not only are there high equipment and labor costs, but product losses due to the several handling operations are also encountered. This processing leaves about 2–3% of the disodium salt of DONS in the product recovered.

In British Pat. No. 1,341,351. there is disclosed an improvement in the conventional process described above. The improved process involves adding to an aqueous sulfonation mixture containing about 10–30% of 2-naphthol-6-sulfonic acid activated carbon, allowing carbon treatment to occur for from about 0.1 to 4.0 hours while maintaining the temperature at 30°–90° C., then filtering off the carbon, adding sodium hydroxide or sodium carbonate to precipitate the sodium salt of 2-naphthol-6-sulfonic acid while maintaining the temperature at from 30°–95° C., filtering off the sodium salt of 2-naphthol-6-sulfonic acid, and washing the filter cake with water. Although this procedure removes BN from the Schaeffer's acid solution, it does not affect the content of DONS therein.

There continues to exist, therefore, the need for an improved process for the preparation of Schaeffer's salt which overcomes the deficiencies of the prior processes and provides a purer product without excessive losses of the desired product. Such a process would fulfill a long-felt need and provide a notable advance in the art.

In accordance with the present invention, there is provided a process for recovering the sodium salt of 2-naphthol-6-sulfonic acid from a sulfonation mixture comprising 2-naphthol-6-sulfonic acid, unreacted 2-naphthol, by-product 6,6'-oxybis(2-naphthalene sulfonic acid) and by-product 2-naphthol-3,6-disulfonic acid, which process comprises: (1) mixing the sulfonation mixture with sufficient water to provide an aqueous solution containing from about 10 to 30 weight percent of 2-naphthol-6-sulfonic acid calculated as the sodium salt; (2) treating the resulting solution for from about 0.1 to 4.0 hours at a temperature between about 30° and 90° C. with sufficient activated charcoal for substantial absorbence of said unreacted 2-naphthol; (3) removing the carbon with its absorbed content of 2-naphthol from the solution; (4) adding sufficient sodium hydroxide or sodium carbonate to the treated solution to provide a pH value of at least about 9.0 so as to precipitate the disodium salt of 6,6'-oxybis(2-naphthalene sulfonic acid) while maintaining the solution at a temperature between about 40° and 100° C.; (5) filtering the precipitated disodium salt of 6,6'-oxybis (2-naphthalene sulfonic acid) from the solution; (6) acidifying the filtrate solution to a pH value in the range of about 2 to 7; (7) precipitating the sodium salt of 2-naphthol-6-sulfonic acid by adding sufficient of a salting-out sodium salt; and (8) recovering the precipitated sodium salt of 2-naphthol-6-sulfonic acid.

The process of the present invention enables high recovery of Schaeffer's Salt to be effected at acceptable purity levels while minimizing processing steps and handling compared to prior procedures. The present process minimizes the content of the disodium salt of 6,6'-oxybis(2-naphthalene sulfonic acid) in the product recovered, an impurity not dealt with by the prior procedures, and thus reduces this impurity level below that previously achieved.

Schaeffer's Salt is the common name for the sodium salt of 2-naphthol-6-sulfonic acid. As indicated, this product is obtained by sulfonation of 2-naphthol and forming the sodium salt of the intermediate 2-naphthol-6-sulfonic acid. In preparing Schaeffer's Salt, 2-naphthol is sulfonated directly with concentrated sulfuric acid at a temperature of about 100° C. under conditions such as to provide the maximum amount of 2-naphthol-6-sulfonic acid and follows conventional procedures. After the sulfonation is substantially complete, the resulting mixture is conventionally referred to as a sulfonation mixture. The sulfonation mixture will contain unreacted 2-naphthol, 2-naphthol-6-sulfonic acid, by-product 6,6'-oxybis(2-naphthalene sulfonic acid) and by-product 2-naphthol-3,6-disulfonic acid, with the major product being 2-naphthol-6-sulfonic acid. Preparation of the sulfonation mixture follows conventional procedure and forms no part of the present invention per se.

In carrying out processing of the sulfonation mixture in accordance with the present invention, the sulfonation mixture is mixed with sufficient water to provide an aqueous solution containing about 10 to 30 weight percent of 2-naphthol-6-sulfonic acid calculated as the sodium salt thereof. It is generally preferable to add the sulfonation mixture to water since concentrated sulfuric acid is generally present in the sulfonation mixture. This particular range of dilution represents a practical range and preferably the content of 2-naphthol-6-sulfonic acid is about 12–20 weight percent, same basis. In the range stated, recovery of Schaeffer's Salt is most effective, while the solution is sufficiently concentrated to minimize the volume of solution handled and yet sufficiently dilute to enable substantial removal of the impurities present.

After the aqueous solution is obtained, the resulting solution is treated with activated carbon to absorb the 2-naphthol present while maintaining the solution at a temperature in the range of about 30° – 90° C. The amount of carbon employed should be sufficient to absorb substantially all of the 2-naphthol, (generally, about 1 – 8 grams of carbon per 100 milliliters of solution, preferably about 2 – 5 grams of carbon, same basis). The carbon treatment is carried out for about 0.1 to 4.0 hours at the temperature stated to ensure substantially complete absorption of 2-naphthol.

After absorption is substantially complete, the treated solution is filtered to remove the carbon and its absorbed content of 2-naphthol therefrom. It is generally desirable to wash the carbon filter cake with small amounts of water to recover any 2-naphthol-6-sulfonic acid entrained therein, adding the wash water to the filtrate. Filter aids may be used to assist filtration. The carbon treatment may be carried out batchwise by adding carbon, and optionally filter aid, to the aqueous solution and filtering as indicated. Alternatively, the carbon treatment may be carried out continuously by passing the aqueous solution through packed columns of carbon. The solution is preferably passed countercurrent to the absorption capacity of the carbon, that is, the incoming solution first contacts the carbon containing the higher content of adsorbed 2-naphthol and the exiting solution contacts the carbon containing the lower content of adsorbed 2-naphthol. The use of a sufficient number of columns of adequate length will provide substantially complete removal of the 2-naphthol for a continuous run of limited duration. However, by providing alternating series of columns, one series can be regenerated with fresh activated carbon while a second series is on stream for treating. By this procedure, the carbon usage can be minimized. Use of the packed carbon columns accomplishes the carbon treatment to remove 2-naphthol and at the same time effects removal of the carbon with its absorbed content of 2-naphthol from the solution, thus conducting steps (2) and (3) of the process as defined.

After the solution is recovered from the carbon treatment, it is substantially free of unreacted 2-naphthol and is processed for further purification prior to recovery of the Schaeffer's Salt. To the thus-recovered solution is added sufficient of sodium hydroxide or sodium carbonate to raise the solution pH above about 9.0, preferably to a pH value of between about 10.0 and 11.0 while maintaining a temperature between about 40° and 100° C. Under these conditions, the disodium salt of 6,6'-oxybis(2-naphthalene sulfonic acid) selectively precipitates without coprecipitation of Schaeffer's Salt. The precipitated disodium salt of 6,6'-oxybis(naphthalene sulfonic acid) is then filtered off and the filter cake is washed with small amounts of water to effect removal of mother liquor and the wash water is combined with the filtrate. After this operation, the filtrate solution is substantially free of the 6,6'oxybis(2-naphthalene sulfonic acid) by-product originally present in the sulfonation mixture, with the unreacted 2-naphthol having been previously removed. Thus, the filtrate solution at this point contains substantially only the 2-naphthol-6-sulfonic acid and the 2-naphthol-3,6-disulfonic acid components of the original sulfonation mixture.

The filtrate solution obtained after removal of the disodium salt of 6,6'-oxybis(2-naphthalene sulfonic acid) is next acidified to a pH in the range of about 2–7, preferably in the range of about 3.5–4.5. Preferably sulfuric acid is employed but other acids may be used and the particular choice is not critical. Maximum precipitation in conjunction with salting occurs within the preferred pH range of purified Schaeffer's Salt, although Schaeffer's Salt of some decrease in quantity and/or quality is obtained over the entire pH range stated.

To the thus-acidified solution is then added a suitable quantity of a salting-out sodium salt to precipitate the Schaeffer's Salt. A salting-out sodium salt is one that will effect precipitation of Schaeffer's Salt typified by sodium chloride, sodium sulfate, and the like. The particular quantity of salt used will vary to some extent, depending upon the particular salt employed. For sodium chloride, for example, about 6 to 12 grams per 100 milliliters of solution is effective. Preferably, a low temperature, such as 20°–40° C. is maintained for carrying out the precipitation. In this manner, the desired Schaeffer's Salt is precipitated from the solution without substantial coprecipitation of 2-naphthol-3,6-disulfonic acid salt.

After the Schaeffer's Salt is precipitated, it is recovered, preferably by filtration. The recovered Schaeffer's Salt is washed with ice water or brine to remove mother liquor containing the R-acid by-product.

By carrying out recovery of Schaeffer's Salt by the process of the present invention, good recovery of Schaeffer's Salt is accomplished and acceptable product purity is obtained while minimizing processing steps compared to the prior art procedures. The product obtained is of sufficient purity to dispense with the added recrystallization purifications previously employed and the attendant product losses associated therewith.

The invention is more fully illustrated by the examples which follow, wherein all parts and percentages are by weight unless otherwise specified.

EXAMPLE 1

2-Naphthol is sulfonated at about 100° C. with 93% sulfuric acid and the sulfonation mass after drowning in water gave 900 mls of solution containing sufficient Schaeffer acid to produce 127 g of Schaeffer's Salt, representing 82% of the theoretical yield based on 2-naphthol used, plus 6.0 g of DONS free acid, 0.8 g of BN, and sufficient R-acid to produce 9.0 g of R-Salt. The solution was heated to 85°–90° C. and treated with 30 g of activated carbon for 1 hour. The solution was then clarified by filtering and the filter cake was washed with sufficient hot water to adjust the total volume of filtrate plus washings to 900 mls. Sufficient 50% sodium hydroxide solution was then added to the filtrate to raise the pH to 10.7 at 90° C., 5.0 g of a diatomaceous earth filter aid was added thereto and the mixture was maintained at 85°–95° C. for ½ hour.

The solution was clarified by filtering and the filter cake was washed with 100 mls of a 6% aqueous solution of sodium chloride. The volume of the combined filtrate plus washings was adjusted to 1100 mls with addition of water and 110 g of sodium chloride was added thereto. The pH of the solution was adjusted to 4.0 by the addition of about 17 mls. of 96% sulfuric acid and the resulting slurry was cooled to 28° C., filtered, washed with 170 mls of cold water and dried.

The product was 113 g of Schaeffer's Salt which contained 0.05% BN, 0.42% R-Salt and 0.51% of disodium salt of DONS on a 100% Schaeffer's Salt basis. The dry weight of recovered Schaeffer's Salt represents an 88% recovery of the Schaeffer's Salt in the sulfonation mixture and an overall yield of 72% of the theoretical Schaeffer's Salt based on the 2-naphthol used in the sulfonation step.

EXAMPLE 2

The procedure of Example 1 was followed up to the point where the volume of the filtrate plus washing solution was adjusted to 1100 mls. The pH of the solution was then adjusted to 4.0 by the addition of 17 mls. of 96% sulfuric acid, 110 g of sodium chloride was added thereto and the slurry was cooled to 28° C. The Schaeffer's Salt was filtered, washed with 190 mls. of cold water and dried.

The product contained 113.6 g of Schaeffer's Salt which analyzed for 0.04% BN, 0.18% R-Salt, and 0.36% of disodium salt of DONS on a 100% Schaeffer's Salt basis.

EXAMPLE 3

The procedure of Example 2 is followed up to the point of addition of 96% sulfuric acid. The pH of the solution is adjusted to 7.0 and the solution is concentrated to give a concentration of about 18 grams of Schaeffer's Salt per 100 mls. and the pH is then adjusted to 4.0 by the addition of 96% sulfuric acid. The solution is cooled to 40° C. and filtered to obtain 111 grams of Schaeffer's Salt which is of excellent quality.

EXAMPLE 4

A Schaeffer sulfonation mixture containing potentially about 7950 parts of Schaeffer Salt, 41 parts of betanaphthol, 584 parts of R-Salt and 328 parts of DONS is drowned into water to give a concentration of about 18 parts of Schaeffer acid (expressed as Na salt) per hundred parts of solution. This solution is passed through two (2) adsorption columns in series, each column containing about 9000 parts of granular activated carbon. After the first column is saturated with beta-naphthol (several batches are processed before the first column is saturated), the first column is regenerated with fresh activated carbon. While this is being done the solution only passes through the second column which contains enough carbon to remove the BN present. When the first column is recharged, the effluent solution from the second column is then passed through the first column until the second column becomes saturated with beta-naphthol, whereupon the solution is then passed through only the first column. After the second column is recharged with fresh activated granular carbon, the effluent solution from the first column is passed through the second column until the first column is again saturated with beta-naphthol.

The carbon-treated acid solution is then treated with about 5300 parts of 50% sodium hydroxide solution at 80°–90° C. to adjust the pH to 10.5–11.0. About 300 parts of filter aid are then added to the batch and the solution is clarified by filtration to remove the disodium salt of DONS.

The solution is then treated with about 1700 parts of 98% sulfuric acid to adjust the pH to 3.5–4.0. About 5000 parts of sodium chloride is added thereto and the resulting slurry is cooled to 25°–30° C. The product is isolated by filtering and washing with cold water. The yield is about 6760 parts of Schaeffer Salt which contains about 0.03% beta-naphthol, 0.1% R-Salt, and 0.5% of disodium salt of DONS.

What is claimed is:

1. A process for recovering the sodium salt of 2-naphthol-6-sulfonic acid from a sulfonation mixture comprising 2-naphthol-6-sulfonic acid, unreacted 2-naphthol, by-product 6,6'-oxybis(2-naphthalene sulfonic acid) and by-product 2-naphthol-3,6-disulfonic acid, which process comprises: (1) mixing the sulfonation mixture with sufficient water to provide an aqueous solution containing from about 10 to 30 weight percent of 2-naphthol-6-sulfonic acid calculated as the sodium salt; (2) treating the resulting solution for from about 0.1 to 4.0 hours at a temperature between about 30° and 90° C. with sufficient activated carbon for substantial absorbence of said unreacted 2-naphthol; (3) removing the carbon with its absorbed content of 2-naphthol from the solution; (4) adding sufficient sodium hydroxide or sodium carbonate to the treated solution to provide a pH value of at least about 9.0 so as to precipitate the disodium salt of 6,6'-oxybis (2-naphthalene sulfonic acid) while maintaining the solution at a temperature between about 40° and 100° C.; (5) filtering the precipitated disodium salt of 6,6'-oxybis (2-naphthalene sulfonic acid) from the solution; (6) acidifying the filtrate to a pH value in the range of about 2 to 7; (7) adding a sufficient amount of sodium chloride or sodium sulfate to precipitate the sodium salt of 2-naphthol-6-sulfonic acid; and (8) recovering the precipitated sodium salt of 2-naphthol-6-sulfonic acid.

2. The process of claim 1 wherein the aqueous solution of step (1) contains 12–20 weight percent of 2-naphthol-6-sulfonic acid calculated as the sodium salt.

3. The process of claim 1 wherein the treatment of step (2) is carried out by passing the solution through packed carbon and step (3) is performed as the solution exits from the packed carbon.

4. The process of claim 1 wherein the pH in step (4) is between about 10.0 and 11.0.

5. The process of claim 4 wherein sodium hydroxide is added in step (4).

6. The process of claim 1 wherein acidification in step (6) is to a pH value in the range of about 3.5 to 4.5.

7. The process of claim 6 wherein the acid employed is sulfuric acid.

8. The process of claim 1 wherein in step (7) the salting-out salt is sodium chloride.

9. The process of claim 1 wherein in step (7) the salting-out salt is sodium sulfate.

10. The process of claim 8 wherein step (7) is carried out at a temperature in the range of about 20°–40° C.

11. A process for recovering the sodium salt of 2-naphthol-6-sulfonic acid from a sulfonation mixture comprising 2-naphthol-6-sulfonic acid, unreacted 2-naphthol, by-product 6,6'-oxybis(2-naphthalene sulfonic acid) and by-product 2-naphthol-3,6-disulfonic acid, which process comprises: (1) mixing the sulfonation mixture with sufficient water to provide an aqueous solution containing from about 10 to 30 weight percent of 2-naphthol-6-sulfonic acid calculated as the sodium salt; (2) treating the resulting solution for from about 0.1 to 4.0 hours at a temperature between about 30° and 90° C. with sufficient activated carbon for substantial absorbence of said unreacted 2-naphthol; (3) removing the carbon with its absorbed content of 2-naphthol from the solution; (4) adding sufficient sodium hydroxide or sodium carbonate to the treated solution to provide a pH value of at least about 9.0 so as to precipitate the disodium salt of 6,6'-oxybis(2-naphthalene sulfonic acid) while maintaining the solution at a temperature between about 40° and 100° C.; (5) filtering the precipitated disodium salt of 6,6'-oxybis(2-naphthalene sulfonic acid) from the solution; (6) acidifying the filtrate to a pH value in the range of about 2 to 7; (7) evaporating a sufficient amount of water from the filtrate to effect precipitation of the sodium salt of 2-naphthol-6-sulfonic acid; and (8) recovering the precipitated sodium salt of 2-naphthol-6-sulfonic acid.

12. A process for recovering the sodium salt of 2-naphthol-6-sulfonic acid from a sulfonation mixture comprising 2-naphthol-6-sulfonic acid, unreacted 2-naphthol, by-product 6,6'-oxybis(2-naphthalene sulfonic acid) and by-product 2-naphthol-3,6-disulfonic acid, which process comprises: (1) mixing the sulfonation mixture with sufficient water to provide an aqueous solution containing from about 10–20 weight percent of 2-naphthol-6-sulfonic acid calculated as the sodium salt; (2) treating the resulting solution for from about 0.1 to 4.0 hours at a temperature between about 30° and 90° C. with sufficient activated carbon for substantial absorbence of said unreacted 2-naphthol; (3) removing the carbon with its absorbed content of 2-naphthol from the solution; (4) adding sufficient sodium hydroxide to the treated solution to provide a pH value in the range of about 10.0 and 11.0 so as to precipitate the disodium salt of 6,6'-oxybis(2-naphthalene sulfonic acid) while maintaining the solution at a temperature between about 40° and 100° C.; (5) filtering the precipitated disodium salt of 6,6'-oxybis(2-naphthalene sulfonic acid) from the solution; (6) acidifying the filtrate to a pH value in the range of about 3.5 and 4.5 with sulfuric acid; (7) maintaining the filtrate at a temperature in the range of about 20° to 40° C. and adding a sufficient amount of sodium chloride to precipitate the sodium salt of 2-naphthol-6-sulfonic acid; and (8) recovering the precipitated sodium salt of 2-naphthol-6-sulfonic acid.

* * * * *